(12) United States Patent
Tsai et al.

(10) Patent No.: US 10,543,988 B2
(45) Date of Patent: Jan. 28, 2020

(54) REAL-TIME MOBILE CARRIER SYSTEM FOR FACILITY MONITORING AND CONTROL

(71) Applicant: TricornTech Taiwan, Taipei (TW)

(72) Inventors: Shih-An Tsai, Nantou (TW); Li-Peng Wang, Taipei (TW); Tsung-Kuan A. Chou, San Jose, CA (US)

(73) Assignee: TricornTech Taiwan, Taipei (TW)

( * ) Notice: Subject to any disclaimer, the term of this patent is extended or adjusted under 35 U.S.C. 154(b) by 0 days.

(21) Appl. No.: 15/496,461

(22) Filed: Apr. 25, 2017

(65) Prior Publication Data

US 2017/0313520 A1 Nov. 2, 2017

Related U.S. Application Data

(60) Provisional application No. 62/329,810, filed on Apr. 29, 2016.

(51) Int. Cl.
*B65G 17/48* (2006.01)
*G01N 1/22* (2006.01)
(Continued)

(52) U.S. Cl.
CPC ......... *B65G 17/485* (2013.01); *G01N 1/2214* (2013.01); *G01N 1/2226* (2013.01);
(Continued)

(58) Field of Classification Search
CPC ...... B65G 17/485; G01N 1/2214; G01N 1/24; G01N 1/2226; G01N 2001/242; G01N 2001/248; H04L 67/12
See application file for complete search history.

(56) References Cited

U.S. PATENT DOCUMENTS

2004/0185551 A1 9/2004 Niehaus
2004/0185554 A1 9/2004 Daitch et al.
(Continued)

FOREIGN PATENT DOCUMENTS

CN 102481858 5/2012
JP 2011-226997 11/2011
(Continued)

OTHER PUBLICATIONS

International Search Report and Written Opinion for PCT Application No. PCT/US2017/029711 dated Jul. 14, 2017, 13 pages.
(Continued)

*Primary Examiner* — Robert R Raevis
(74) *Attorney, Agent, or Firm* — Womble Bond Dickinson (US) LLP

(57) ABSTRACT

Embodiments of a mobile carrier monitoring apparatus are disclosed. The apparatus includes one or more mobile carriers configured to receive items being manufactured in its interior and configured be moved by a transport system to multiple positions within a manufacturing facility. A mobile carrier control system is positioned in the interior or on the exterior of each mobile carrier, as are one or more sensors that are coupled to the mobile carrier control system. A communication system is positioned in the interior or on the exterior of each mobile carrier and communicatively coupled to the at least one sensor and to the mobile carrier control system, and an electrical power system positioned in the interior or on the exterior of each mobile carrier and coupled to deliver electrical power to the mobile carrier control system, to the one or more sensors, and to the communication system. Other embodiments are disclosed and claimed.

10 Claims, 12 Drawing Sheets

(51) Int. Cl.
  *G01N 1/24*    (2006.01)
  *H04L 29/08*   (2006.01)
(52) U.S. Cl.
  CPC ......... *G01N 1/24* (2013.01); *G01N 2001/242* (2013.01); *G01N 2001/248* (2013.01); *H04L 67/12* (2013.01)

(56) References Cited

U.S. PATENT DOCUMENTS

| | | |
|---|---|---|
| 2007/0198282 A1 | 8/2007 | Williams et al. |
| 2009/0299582 A1 | 12/2009 | Anderon |
| 2010/0156171 A1 | 6/2010 | Sechrist |
| 2013/0292512 A1 | 11/2013 | Erben et al. |
| 2017/0183154 A1* | 6/2017 | Kinugawa ............ B65G 1/0457 |

FOREIGN PATENT DOCUMENTS

| | | |
|---|---|---|
| KR | 20000065367 | * 11/2000 |
| TW | M501823 | 6/2015 |
| WO | WO-2011/028703 | 3/2011 |

OTHER PUBLICATIONS

Office Action for Taiwan Patent Application No. 106114333 dated Mar. 19, 2018, 9 pages.

Office Action for Taiwan Patent Application No. 106114333 dated Nov. 14, 2018, 15 pages.

\* cited by examiner

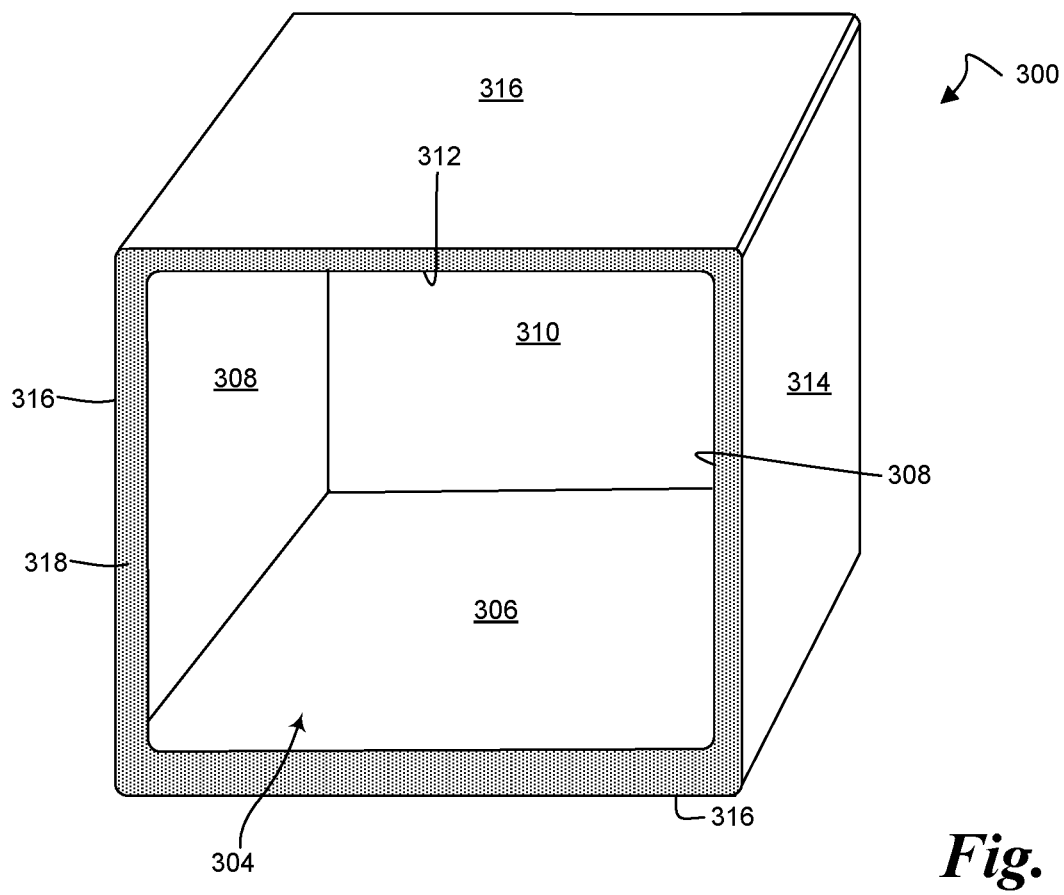
Fig. 3
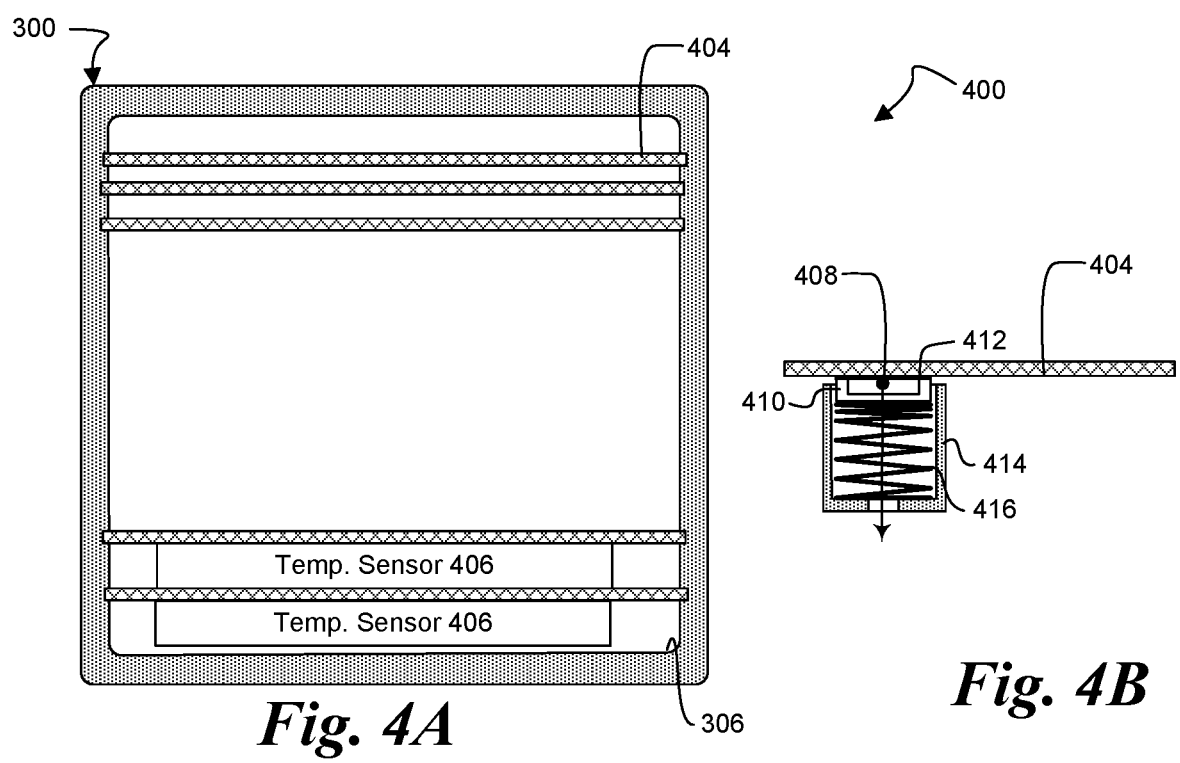
Fig. 4A
Fig. 4B

REAL-TIME MOBILE CARRIER SYSTEM FOR FACILITY MONITORING AND CONTROL

CROSS-REFERENCE TO RELATED APPLICATIONS

This application claims priority under 35 U.S.C. § 119(e) to U.S. Provisional App. No. 62/329,810, filed 29 Apr. 2016, which is hereby incorporated by reference in its entirety.

TECHNICAL FIELD

The disclosed embodiments relate generally to facility monitoring and in particular, but not exclusively, to a real-time mobile carrier system for facility monitoring and control.

BACKGROUND

Business or factory internal monitoring systems are generally large and stationary machines and detection systems, which limits their detection range to the region immediately surrounding their location. Many of these detectors would be needed to adequately cover a large facility, but that would be expensive and would take up floor space that might be needed by, or better used for, other equipment.

BRIEF DESCRIPTION OF THE DRAWINGS

Non-limiting and non-exhaustive embodiments of are described below with reference to the following figures, wherein like reference numerals refer to like parts throughout the various views unless otherwise specified.

FIG. 3 is a three-dimensional diagram of an embodiment of a bare mobile carrier without sensors or a collection system.

FIGS. 4A-4C are block diagrams of embodiments of a mobile carrier including one or more temperature monitoring sensors.

DETAILED DESCRIPTION OF THE ILLUSTRATED EMBODIMENTS

Figure 1A:
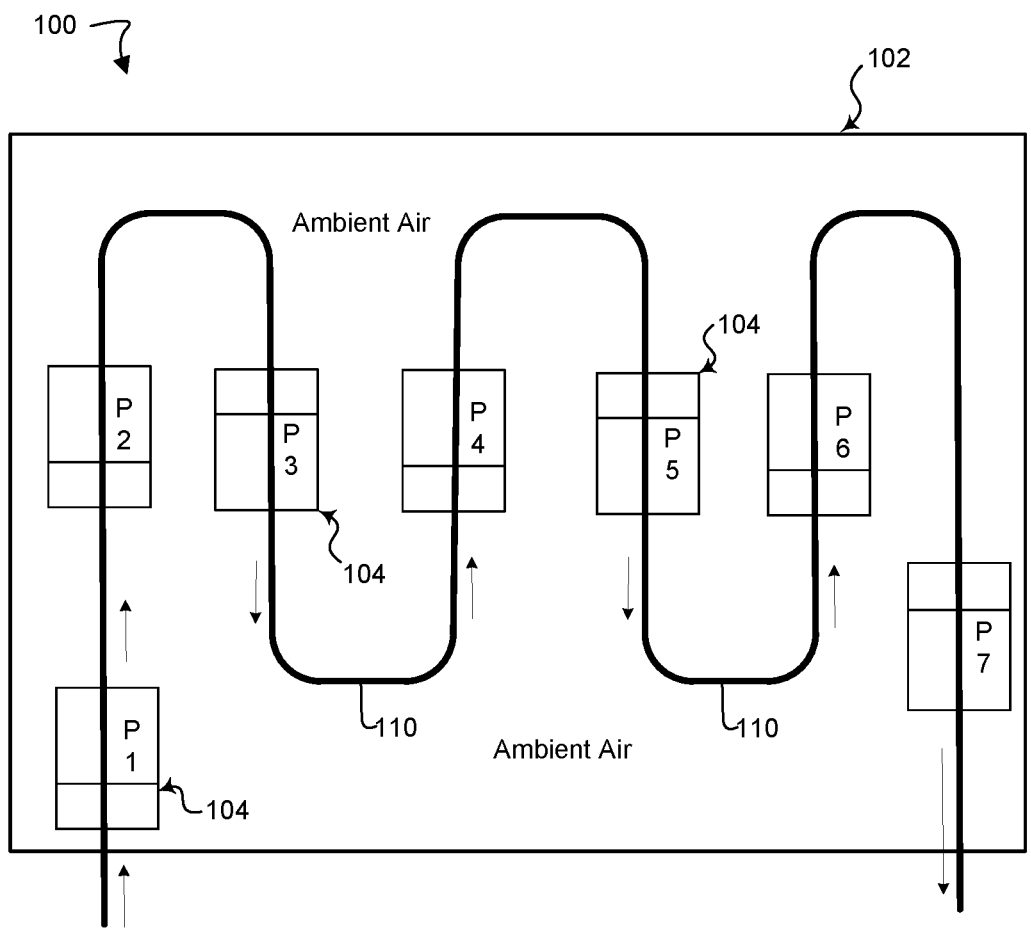
FIGS. 1A-1B are drawings of an embodiment of mobile carrier system for monitoring a semiconductor fabrication facility.

Embodiments are described of an apparatus, system, and method for a real-time facility monitoring and control using mobile carriers. Specific details are described to provide an understanding of the embodiments, but one skilled in the relevant art will recognize that the invention can be practiced without one or more of the described details or with other methods, components, materials, etc. In some instances, well-known structures, materials, or operations are not shown or described in detail but are nonetheless encompassed within the scope of the invention.

Reference throughout this specification to "one embodiment" or "an embodiment" means that a described feature, structure, or characteristic can be included in at least one described embodiment. As a result, appearances of "in one embodiment" or "in an embodiment" do not necessarily all refer to the same embodiment. Furthermore, the particular features, structures, or characteristics may be combined in any suitable manner in one or more embodiments.

Disclosed below are embodiments of a mobile carrier system that can be used in a factory internal monitoring system with multiple detection systems. The disclosed embodiments extend the detection range and increase automated applications. In addition, in some embodiments the mobile carrier system can be used with a smart station; this smart station provides central control, data transmission, power charging, and modular replacement methods. It increases the mobile carrier system's usability and includes more detection items or detection systems.

Embodiments of a mobile carrier system can include a detection system or/and a power system or/and a wireless or wired communication transmission system or/and a set of modular input and output connection system. Embodiments of a smart station can include a set of modular input and output connection system or/and a power supply system or/and a wireless or wired communication transmission system or/and a station operating system or/and a set of detection systems.

Embodiments of the mobile carrier system can be used with multiple detection systems. In one embodiment, the mobile carrier system moves along a transmission path or track to different locations to get the specific measuring point data. It can also move to a specific location and deliver the mobile carrier's detection system to the equipment, so that the detection system performs the measurement for the equipment. Embodiments of the mobile carrier system can also move to a specific location, collect data, or material such as an analyte, from inside or outside the carrier into the carrier system, and carry the analyte to a specific analysis machine for measurement.

Embodiments of the mobile carrier system can operate with a self-built (i.e., on-board or self-contained) power system. When the self-built power system need to be charged, the carrier system can move to a smart base station and the base station can provide power supply and charging. Embodiments of mobile carrier system detect and control by a wireless or wired communication transmission system that can transmit data or control messages to a central control system for data analysis and processing. The output from the central control system can be provided to a system administrator or user, who can then use the integrated information to decide a corresponding method or strategy.

Embodiments of the mobile carrier system and smart station can be connected by a modular input/output (I/O) coupling system. Every modular coupling in the I/O coupling system provides the different I/O function such as Ethernet, one or more tubes through which analyte or gas sample can be transferred between the smart base station and the mobile carrier, and so on. The modular I/O coupling system provides convenient replacement, can reduce the design change time, and can also help users design their own systems quickly. The smart base station can be integrated with multiple detection systems (see below). The analytes carried from the mobile carrier system can be detected by the equipment in the smart station.

Figure 1B:
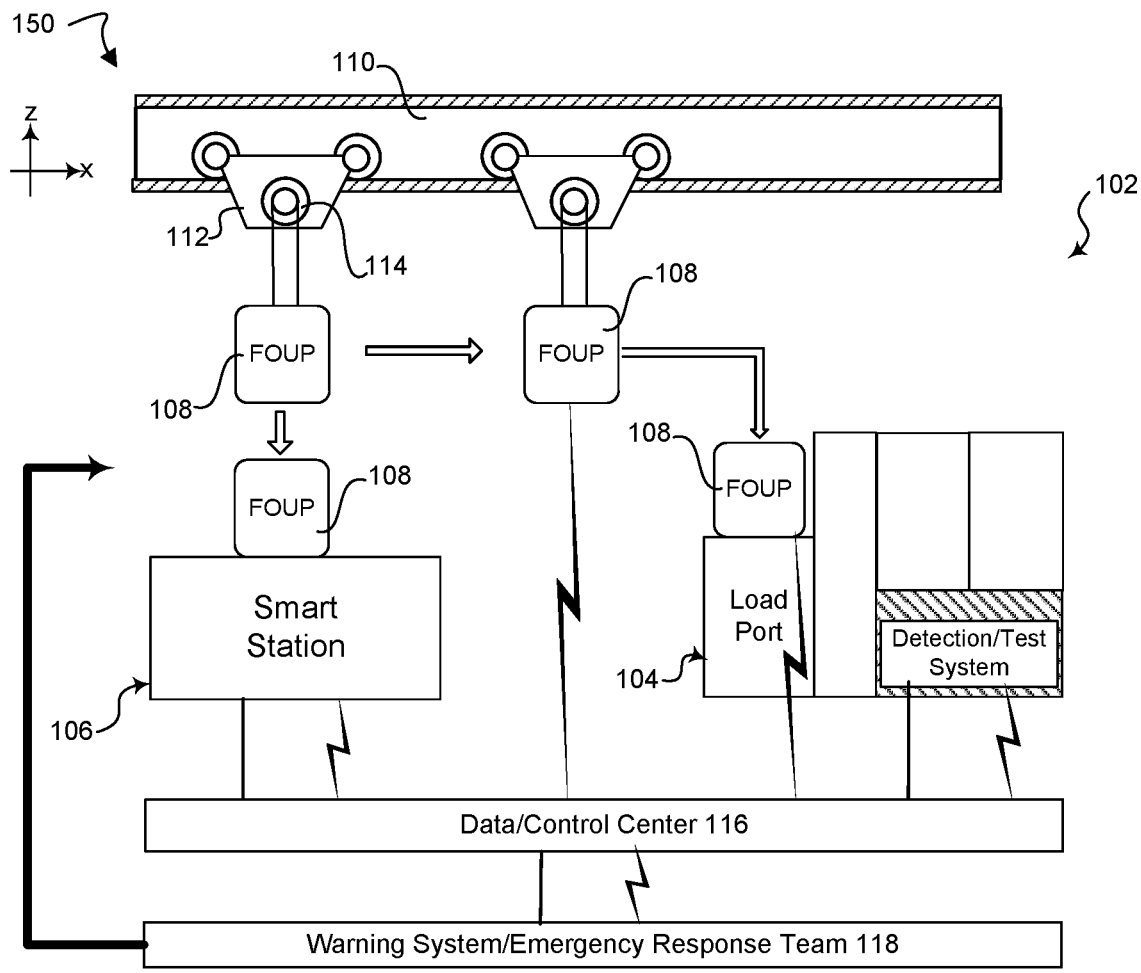

FIGS. 1A-1B together illustrate an embodiment of a mobile carrier system for monitoring a manufacturing facility 100. Manufacturing line 100 can be used in semiconductor fabrication, for instance, but in other embodiments could be used for other purposes and with different equipment than shown.

FIG. 1A illustrates a general layout of manufacturing line 100. Manufacturing line 100 is positioned in an enclosure 102, which can be a building, a room or bay within a building, or some other type of enclosure. One or more process equipment modules 104 are positioned within enclosure 102. Each process equipment module 104 includes a load port and can include one or more chambers, each of which performs different functions related to the manufacturing steps carried out by that particular process equipment module.

Manufacturing processes generally involve many steps, and each process equipment module performs only some of the steps in the overall manufacturing process. As a result, the items being manufactured on manufacturing line 100—semiconductor wafers with processors, memories, MEMS chips, optical chips, etc., in a semiconductor manufacturing facility—must be moved from one process equipment module to another until all the steps in the process are performed. Track 110 winds through facility 102 to transport mobile carriers 106 (see FIG. 1B)—and hence items being manufactured, which are carried inside the mobile carriers—to multiple process equipment modules; the illustrated embodiment has seven processing equipment modules 104 labeled P1-P7, but other embodiments can have a different number. After the items being manufactured move through all the process equipment modules 104 in a particular enclosure 102, the transport system exits enclosure 102 with the movable carrier.

FIG. 1B illustrates an embodiment of a mobile carrier system 150 for monitoring manufacturing line 100. Items being manufactured are moved around the factory using mobile carriers 108 that carry the items being manufactured inside, often in a sealed micro environment. The mobile carrier monitoring system uses the same mobile carriers 108 used to transport the items being manufactured to also transport sensors, analyzers, and sampling devices that can be used to monitor conditions in the manufacturing facility. In different embodiments, mobile carriers 108 can carry only sensors and/or sampling devices, or can carry both items being manufactured and sensors and/or sampling devices. In a semiconductor facility embodiment such as the one shown, mobile carriers 108 are called Front-Opening Unified Pods (FOUPs), wafer containers, or substrate containers, because they are used to transport semiconductor wafers. But in other embodiments other types of movable carrier can be used.

A transport system carries each mobile carrier 108 around the manufacturing facility from the load port of one process equipment module 104 to the load port of another, so that different manufacturing steps can be performed on the items carried inside each movable carrier. In the illustrated embodiment, the transport system is an overhead track-and-hoist system. Wheeled and motorized carriages 112 run along a track 110. A hoist 114 is mounted to each wheeled carriage 112 to lift mobile carriers 108 in the z direction and also potentially move them in the y direction (i.e., into and out of the page) so that mobile carriers 108 can be placed on load ports that can accommodate multiple carriers. Other embodiments of the mobile carrier system can get their mobility from other systems such as automatic transport systems, automatic guided vehicles (AGVs), overhead hoist transfer and Front Opening Unified Pod (OHT & FOUP), unmanned flying vehicles (UFV), and other mobility systems used in the semiconductor industry, panel industry, logistics and so on.

In monitoring system 150, one or more mobile carriers 108 can each be configured to have one or more sensors, a sampling system, or both a sampling system and sensors, positioned in their interior or on their exterior. The sensors and sampling systems can be used to detect, measure, or otherwise characterize, quantitatively or qualitatively, conditions inside or outside the mobile carriers as they are moved around facility 102 by the transport system.

Each mobile carrier 108 can be mated with a smart station 106 (see FIG. 2) or with the load ports of process equipment modules 104 in the facility. Each mobile carrier 108 can communicate, by wire or wirelessly, with a central data/control center 116 that monitors the overall conditions in facility 102 as it receives data from the one or more mobile carriers. Smart station 106 and process equipment module 104 can also communicate, wirelessly or by wire, with data/control center 116, so that when a mobile carrier is mated to smart station 106 or to process equipment module 104, the data from sensors or samplers in mobile carriers 108 can be transmitted to the data/control center by the smart station or the process equipment module instead of directly by the mobile carrier itself. Data/control center 116 can communicate, also wirelessly or by wire, with a warning system or emergency response team 118 so that they can be sent into the factory to follow up if abnormal conditions are detected. Data/control center 116 can also communicate, also wirelessly or by wire, with process equipment modules to send control signals that can adjust the processes in response to the monitoring measurements.

Figure 2:
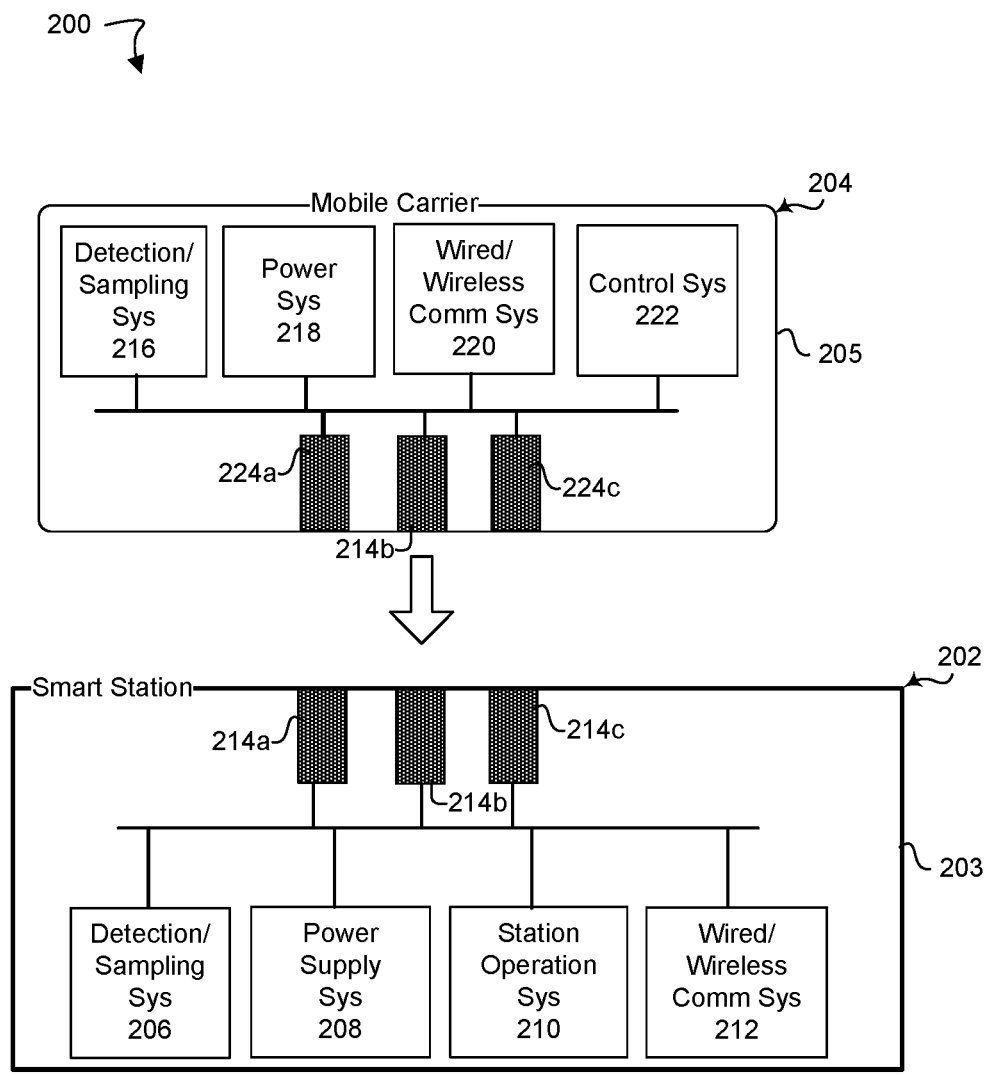
FIG. 2 is a drawing of an embodiment of a monitoring system using mobile carriers.

FIG. 2 illustrates embodiments of a monitoring system 200 that includes a smart station 202 and a mobile carrier 204. In one embodiment smart station 202 can be stationary, but in other embodiments it can be made mobile, for instance by housing it in a cabinet with wheels.

Smart station 202 includes a housing 203 within which are located a detection and/or sampling system 206, a power supply system 208, a station operation system 210, and a wired or wireless communication system 212. Detection and/or sampling system 206, power supply system 208, station operation system 210, and wired or wireless communication system 212 are all coupled to a modular coupling system 214 designed to be compatible with a modular coupling system 224 on mobile carrier 204. The illustrated embodiment has a bus-type coupling between the components and modular coupling system 214, but in other embodiments these couplings can be done differently and need not be a bus.

Detection and/or sampling system 206 is positioned within smart station 202 and is coupled to at least one individual coupler of modular coupling system 214. The detection and/or sampling system 206 can be a detection system, a sampling system, or both a detection system and a sampling system. For detection, system 206 can include detectors or analyzers to detect, measure, or otherwise characterize, quantitatively or qualitatively, conditions inside or outside the smart station or conditions at locations were mobile carrier 204 has sampled its environment as it moved around facility 102. Any of the detectors discussed below for use in embodiments of mobile carrier 204 can also be used in embodiments of smart station 202. When detection and/or sampling system 206 operates as a sampling system, it can sample the environment around smart station 202 and can then analyze the sample using a detector or analyzer within the smart station itself, or it can transfer the collected sample, via modular coupling system 214, to a mobile carrier 204, which can then use its detection system for analysis. In one embodiment, sampling system 206 can be similar to the sampling system described below for FIGS. 13-14.

Power supply system 208 is positioned within smart station 202 and is coupled to at least one individual coupler within modular coupling system 214. The power supply system can provide electrical power to other components within smart station 202 and can also be used to either directly power components within mobile carrier 204 when the mobile carrier is docked on the smart station, or to charge the mobile carrier's own power system, in this case power system 218. In an embodiment, power supply system 208 can also be coupled to an external power supply (not shown), for instance the electrical power supply of the facility in which the smart station is located.

Station operating system 210 is positioned within smart station 202 and is coupled to the other components within smart station 202—detection and/or sampling system 206, power supply system 208, and wired or wireless communication system 212 in this embodiment—as well as being coupled to at least one individual coupler in modular coupling system 214. In one embodiment, the hardware of station operating system 210 can be a general-purpose computer including a processor, memory, storage, and so on, together with software having instructions that allow it to exchange data with, and control the functions of, the other components within the smart station, as well as communicate with a mobile carrier when it is docked on the smart station. Station operating system 210 can also be used to receive, process, and/or interpret data received from other components within smart station 202 or from components within mobile carrier 204. In other embodiments, station operating system 210 can be a special-purpose computer such as an application specific integrated circuit (ASIC), also with software having instructions that cause it to perform the required functions.

Wired/wireless communication system 212 is positioned within smart station 202 and is coupled to the other components within smart station 202—detection and/or sampling system 206, power supply system 208, and station operating system 210 in this embodiment—as well as being coupled to at least one individual coupler in modular coupling system 214. Wired/wireless communication system 212 can communicate with other components within smart station 202 to exchange data with other components, and can also communicate with communication system 220 when mobile carrier 204 is docked on smart station 202, to exchange data with the mobile carrier. Communication system 212 can also be communicatively coupled, by wire or wirelessly, to exchange data with other external components, such as a data/control system 116 (see FIG. 1B).

Modular coupling system 214 is used to couple components within smart station 202 to components within mobile carrier 204 when a mobile carrier is docked on the smart station. As such, modular coupling system 224 of the mobile carrier will be substantially compatible with modular coupling system 214, with each individual coupler of modular coupling system 214 having a counterpart individual coupler for the same function within modular coupling system 224. In the illustrated embodiment, coupling system 214 includes three couplings 214a-214c, but in other embodiments can include a different number of couplings. The individual couplers in coupling system 214 can include electrical couplings, fluid couplings, communication couplings, or mechanical couplings. For instance, in one embodiment one individual coupler 214, and hence a corresponding coupler 224, can be for communication while another individual coupler can be a fluid coupling that allows transfer of a fluid sample from sampling system 216 to detection system 206. In another embodiment, one individual coupler 214, and hence a corresponding coupler 224, can be mechanical couplers that keep mobile carrier 204 firmly in place when docked on smart station 202. In still other embodiment, individual couplers can have multiple functions; for instance, a pair of individual couplers could function as both a fluid coupling and a mechanical coupling. Modular coupling systems 214 and 224 allow quick connection and disconnection compared to a traditional connection interface.

Mobile carrier 204 has a set of components similar to smart station 202. The components are positioned within a housing 205, which is essentially a mobile carrier used in the manufacturing process (see FIG. 3). In the illustrated embodiment, each component in smart station 202 has a corresponding component in mobile carrier 204: the components in mobile carrier 204 include a detection and/or sampling system 216, a power supply system 218, a control system 220, and a wired or wireless communication system 220. But other embodiments of mobile carrier 204 need not have a set of components corresponding to the components in smart station 202. In some embodiments mobile carrier 204 can be a dedicated monitoring system—that is, it can carry only the components that make up the monitoring system but no items being manufactured. But in other embodiments it can carry both a monitoring system and items being manufactured.

In mobile carrier 204, detection and/or sampling system 216 has the same functions, and can include similar components to detection/sampling system 206; control system 222 has the same functions, and can include similar components, as station operating system 210; and wired or wireless communication system 220 has the same functions, and can include similar components as wireless communication system 212. In one embodiment, the primary difference is in power system 218. Because mobile carrier 204 is mobile, in one embodiment power system 218 is a self-contained power system, such as a rechargeable or replaceable battery, rather than a power system that derives its power from an external source such as the facility's electrical power source. And in embodiments where power system 218 is self-contained, it would be desirable to choose the other components in mobile carrier 204 to have lower power consumption that their analogous counterparts in smart station 202.

As in smart station 202, the components of mobile carrier 204 are coupled to a modular coupling system 224 designed to be compatible with a modular coupling system 214 on smart station 202. In the illustrated embodiment, coupling system 224 includes three couplings 224a-224c, but in other embodiments can include a different number of couplings. The individual couplers in coupling system 224 can also include electrical couplings, fluid couplings, communication couplings, or mechanical couplings. In the illustrated embodiment, the number of individual couplers 224 matches the number of individual couplers 214, but in other embodiments the numbers of couplers need not match exactly, so long as any individual coupler that does not find a corresponding coupler in the other is not needed.

FIG. 3 illustrates an embodiment of a bare mobile carrier 300—that is, a mobile carrier without any of the components shown in FIG. 2. In effect, then, bare mobile carrier 300 is housing 205 within which the components of the monitoring system are put (see FIG. 2). Mobile carrier 300 is a hexahedron, a cube in this case, but in other embodiments it can have a different shape such as cylindrical, triangular, etc. Mobile carrier 300 has an exterior including top and bottom exterior surfaces 316 and side surfaces 314. A single interior chamber 304 can be used to house items being manufactured and the monitoring system components shown in FIG. 2, as described below, but other embodiments of mobile carrier can include multiple interior chambers. Interior chamber 304 is bounded by floor 306, walls 308, back wall 310, and ceiling 312. Sidewalls 318 occupy the space between exterior surfaces and interior walls of mobile carrier 300; the sidewalls can be solid, hollow, insulated, or used to house components or connections between components. Mobile carrier 300 can also include a door (not shown) that attaches to the front using hinges mounted on one of sidewalls 318 to close off interior chamber 304. The door can seal the interior chamber 304, hermetically or not hermetically, from the outside environment.

Figure 11:
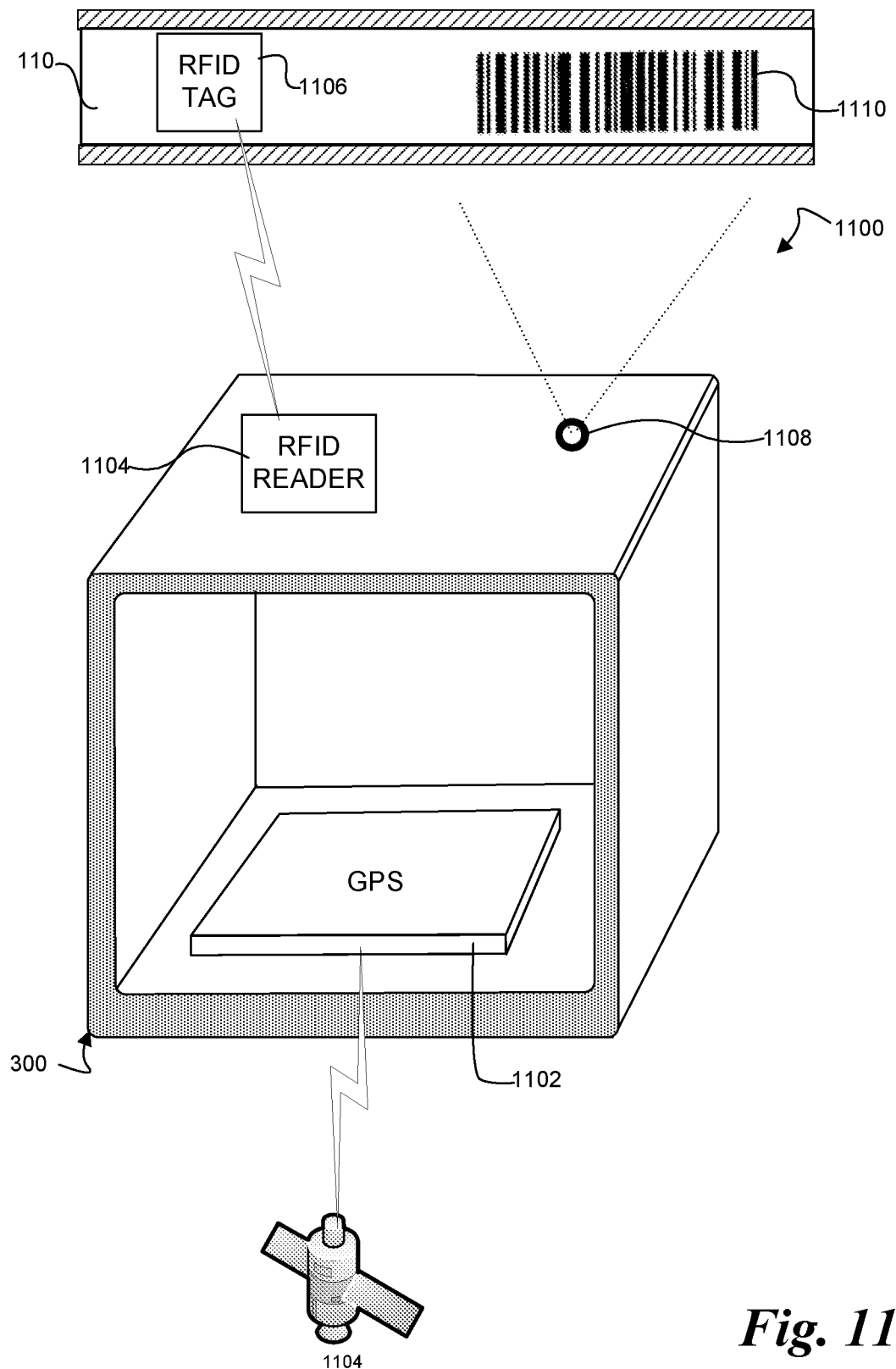
FIG. 11 is block diagram of an embodiment of a mobile carrier including one or more location monitoring sensors.
Figure 12A:
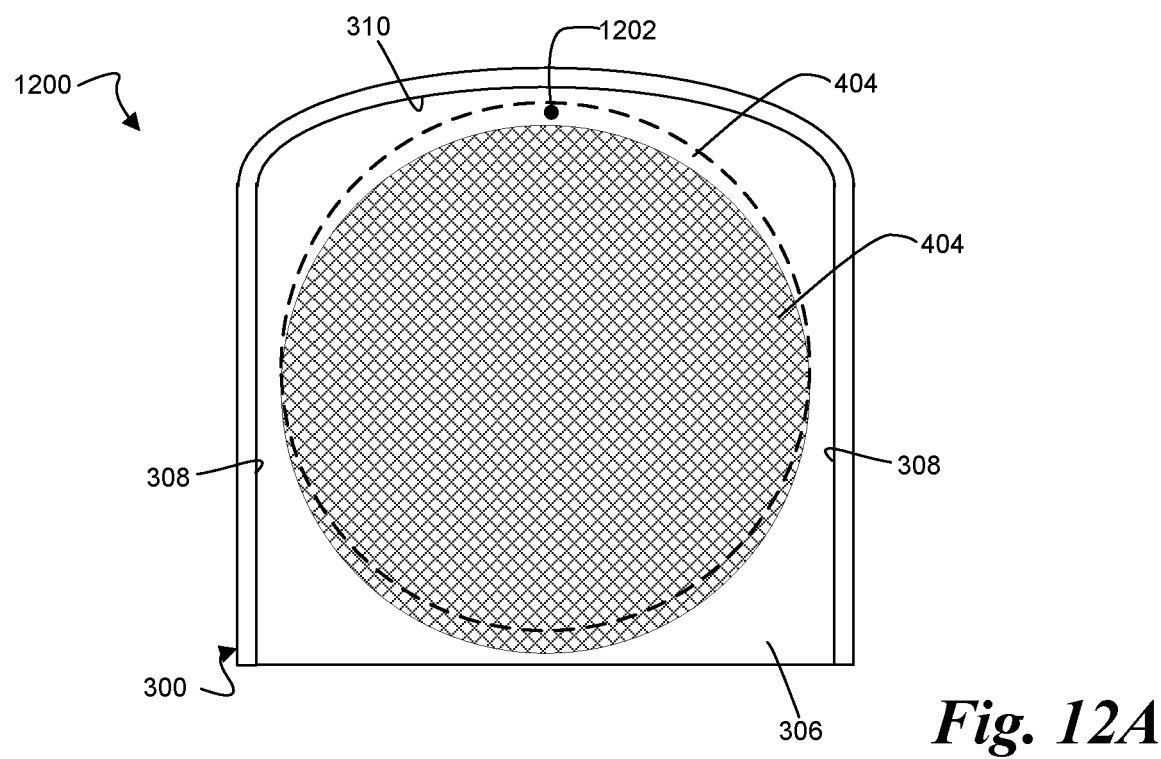
FIGS. 12A-12B are block diagrams of an embodiment of a mobile carrier including one or more internal position monitoring sensors.
Figure 12B:
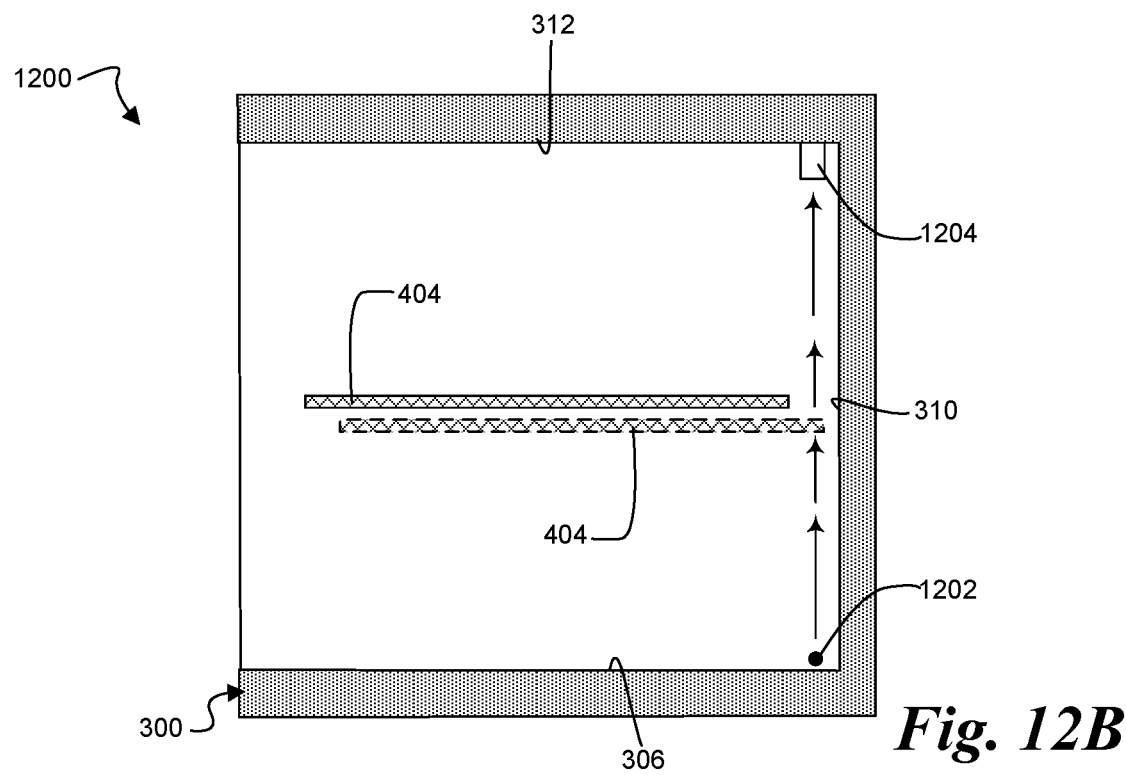
Figure 13:
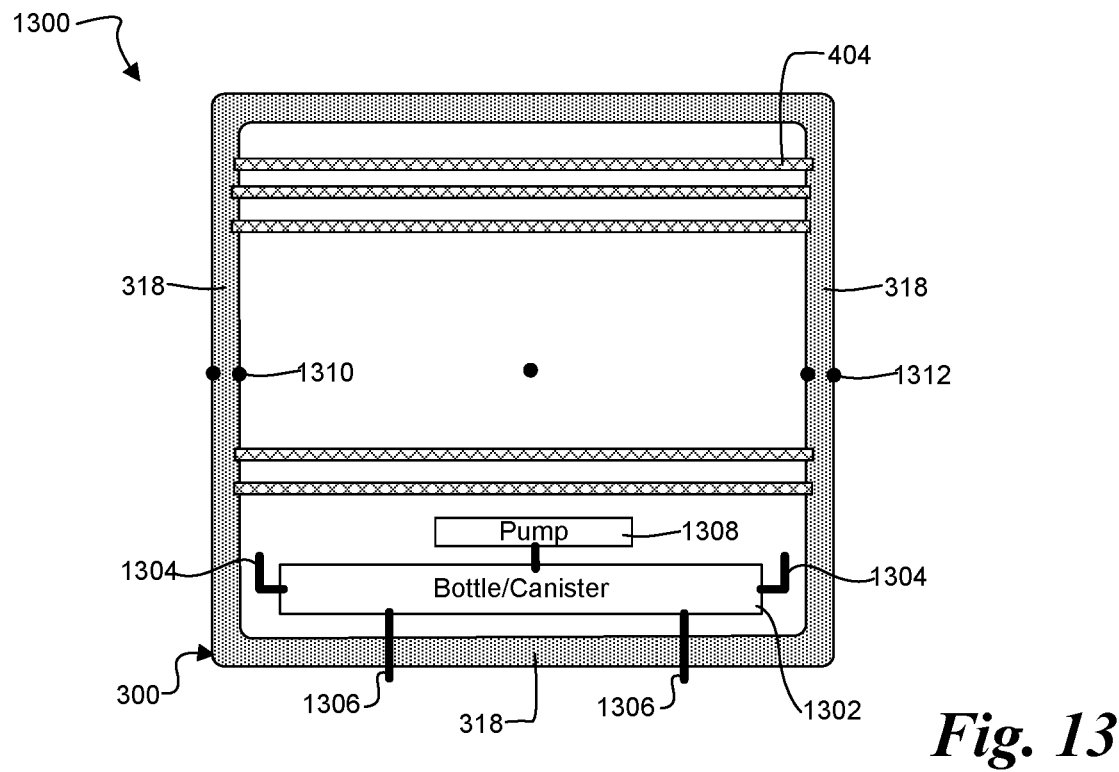
FIG. 13 is block diagram of an embodiment of a mobile carrier including a sample collection system.
Figure 14:
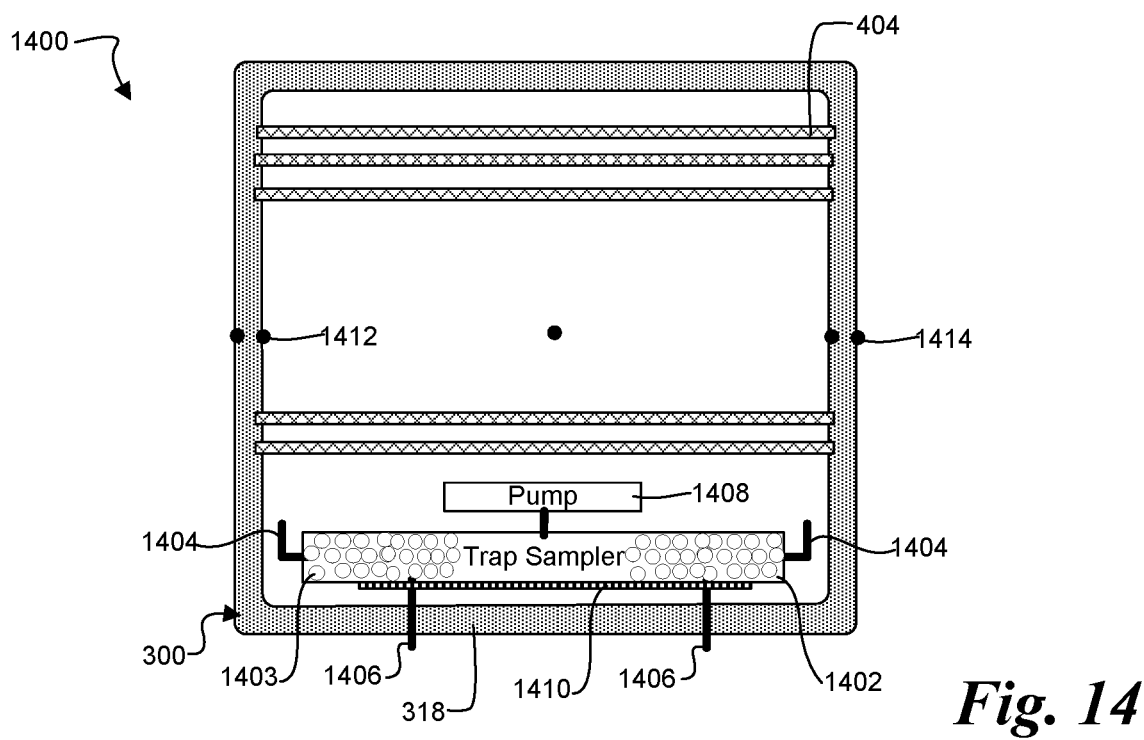
FIG. 14 is block diagram of another embodiment of a mobile carrier including a sample collection system.

FIGS. 4A-14 describe embodiments of mobile carriers with different types of detection systems, sampling systems, or detection systems and sampling systems. In these figures, only the detection/sampling system is shown to avoid cluttering the drawing, but of course other components of a mobile carrier, as shown in FIG. 2 and discussed above, as well as any needed interconnections between components, will be present even though not shown. And, although they are described individually, the described sensors need not be used in isolation, but can be used in any combination. For instance, a mobile carrier could pair one or more of the sensors in FIGS. 4A-12B together with a sampling system as shown in FIGS. 13-14. Finally, the mobile carriers illustrated in these figures are shown and described in the context of a mobile carrier used for semiconductor manufacturing, such as a FOUP, but in other embodiments a different type of carrier can be used.

FIGS. 4A-4B illustrate an embodiment of a mobile carrier 400 including one or more temperature monitoring sensors. In mobile carrier 400, one or more semiconductor wafers 404 are stacked in the interior of mobile carrier 300 for transport between process equipment modules. Temperature sensors 406 are positioned in the interior of the mobile carrier to measure the temperature of the wafers. In the illustrated embodiment, a temperature sensor is positioned on floor 306 to measure the temperature of the bottom-most wafer, and thereafter one or more temperature sensors 406 can be positioned between wafers to measure the temperature of the wafer above. In some embodiments only the temperature of a single wafer 404, or a number of wafers smaller than the capacity of the carrier, can be measured, but in other embodiments the temperature of every wafer can be measured.

FIG. 4B illustrates an embodiment of a mechanism by which temperature sensors 406 can measure the temperature of a wafer. A temperature probe 408 is positioned inside a slider 410 and in thermal contact with a thermally conductive pad 412. Slider 410 is held within sleeve 414 and can move up and down relative to the sleeve. A low-force spring 416 is also held within sleeve 414 and is used to push slider 410 toward wafer 404 so that pad 412 is in contact with the wafer. Temperature probe 408 then measures the temperature of wafer 404 through thermally conductive pad 412 and transmits its readings to processing circuitry via a wire connection between probe 408 and the circuitry.

Figure 4C:
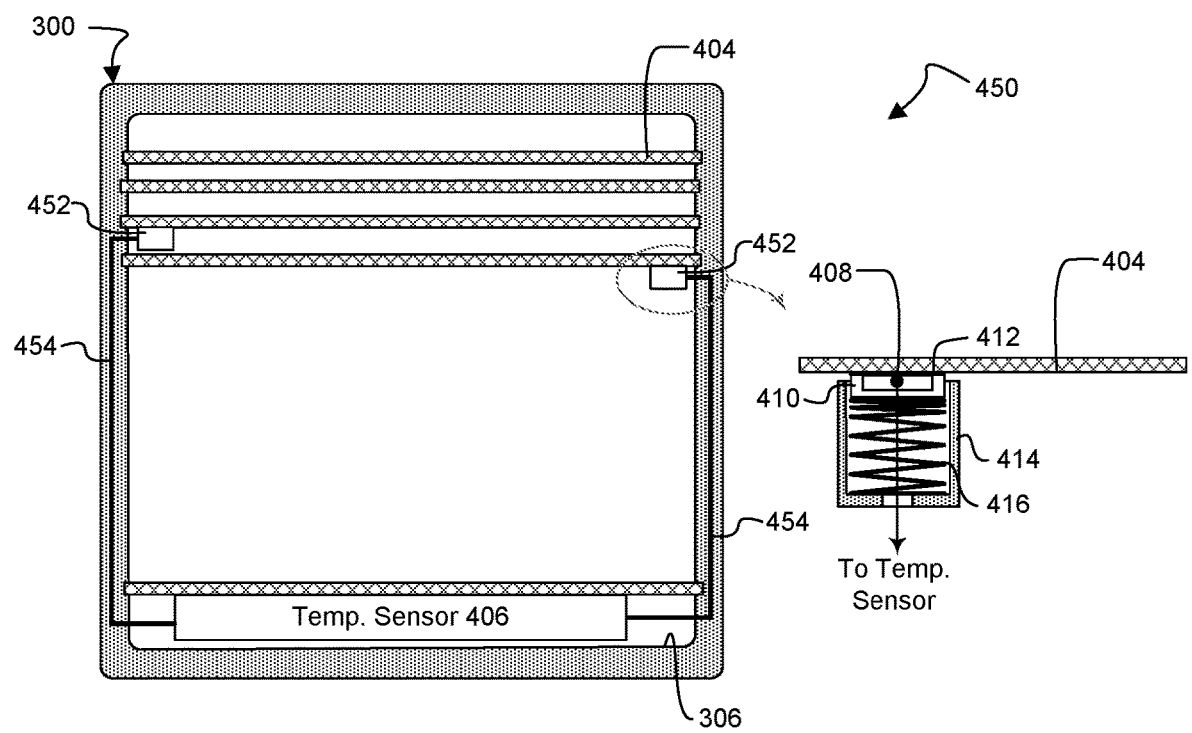

FIG. 4C illustrates an embodiment of a mobile carrier 450 including a temperature monitoring sensor. Mobile carrier 450 is in many respects similar to mobile carrier 400. In mobile carrier 450, one or more semiconductor wafers 404 are stacked in the interior of mobile carrier 300 for transport between process equipment modules. The primary difference between mobile carriers 450 and 400 is that mobile carrier 450 includes a single temperature sensing module positioned 406 in the mobile carrier near floor 306. Temperature sensing module 406 is coupled by wires 454 to multiple temperature sensing probes 452 located at multiple wafers 404. In the illustrated embodiment wires 454 are routed through the sidewalls 318 of mobile carrier 300, but other arrangements could route the wires differently than shown, for instance along the exterior of the carrier. In the illustrated embodiment. temperature sensing probes 452 can be the same probe described in FIG. 4B, but can be a different kind of probe in other embodiments. With this arrangement, temperature sensing module 406 can detect the temperature of multiple wafers in the carrier, up to and including every wafer in the carrier.

Figure 5:
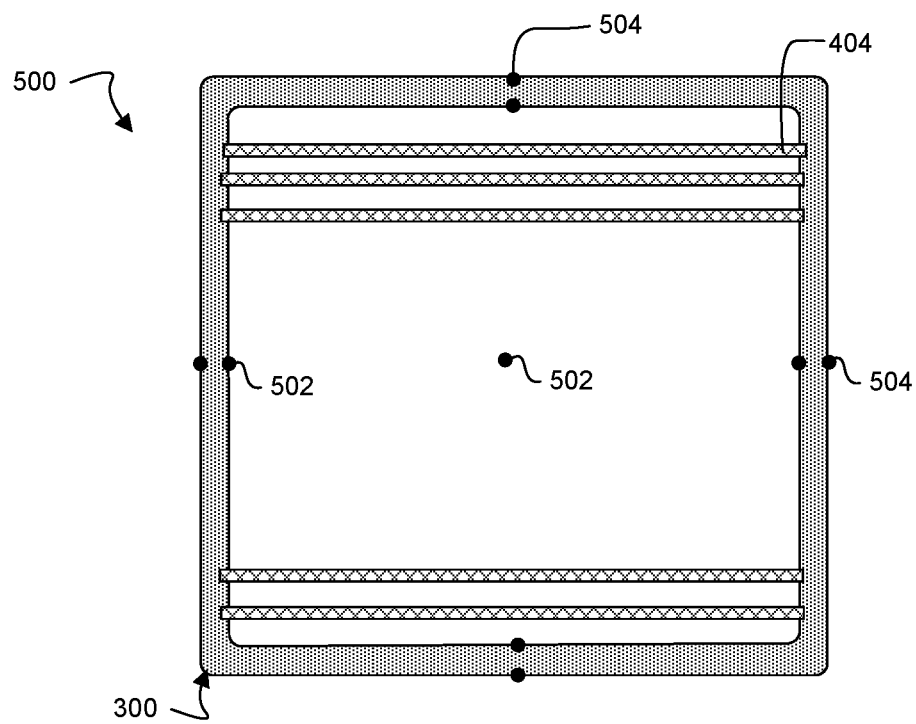
FIG. 5 is block diagram of an embodiment of a mobile carrier including one or more airflow monitoring sensors.

FIG. 5 illustrates an embodiment of a mobile carrier 500 including one or more airflow monitoring sensors. In mobile carrier 500, one or more semiconductor wafers 404 are stacked in the interior of mobile carrier 300 for transport between process equipment modules. Airflow sensors 502 are positioned in the interior of the carrier to measure airflow quantities, such as direction and speed, within the interior. In the illustrated embodiment, airflow sensors 502 are positioned on the floor, ceiling, walls, and back wall, but other embodiments need not position airflow sensors on every interior wall and other embodiments can use more or less airflow sensors than shown. Airflow sensors 504 can also be positioned on the exterior bottom, top, and side surfaces of the carrier to measure airflow quantities, such as direction and speed, outside mobile carrier 400 or in or near process equipment with which mobile carrier 400 has been mated. Other embodiments need not position airflow sensors on every exterior surface, and other embodiments can use more or less airflow sensors than shown. In one embodiment, air flow sensors can monitor the air flow in the carrier when it is docked on the load port of a process equipment module during a carrier air purge/clean process. The flow information can be used to adjust the purge air flow pressure or total volume to achieve an optimum mobile carrier cleaning process.

Figure 6:
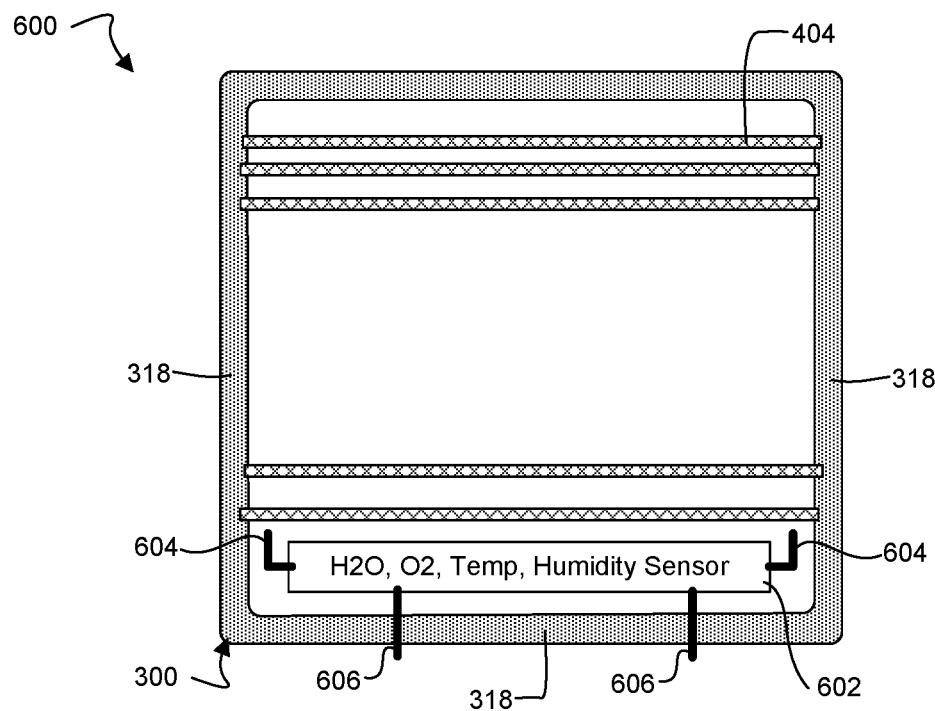
FIG. 6 is block diagram of an embodiment of a mobile carrier including one or more humidity, oxygen, water, and/or temperature monitoring sensors.

FIG. 6 illustrates an embodiment of a mobile carrier 600 including a humidity, oxygen, water and/or temperature monitoring sensors. In mobile carrier 600, one or more semiconductor wafers 404 are stacked in the interior of mobile carrier 300 for transport between process equipment modules. An H₂O (water), oxygen, temperature, or humidity sensor 602 is positioned in the interior of the carrier, on or near the floor of the carrier.

Sensor 602 includes sampling tubes 604 fluidly coupled to the sensor and to the interior of the carrier to draw in air from the interior of the carrier for measurement. Sensor 602 also includes sampling tubes 606 that extend through the bottom sidewall to fluidly couple the sensor and to the exterior of the mobile carrier so that it can draw in air from the exterior of the carrier for measurement—for instance ambient air from the facility or air from a process equipment module to which the carrier 600 was coupled. The sensor can thus detect the H₂O/oxygen/temperature and humidity conditions inside the carrier or in a machine or in the environment outside the carrier. In other embodiments the routing of the internal and external sampling tubes can be different than shown— sampling tubes 604 or 606 could be routed through the sidewalls 318 of carrier 300, for instance, and other embodiments need not sample both internal and external air.

Figure 7:
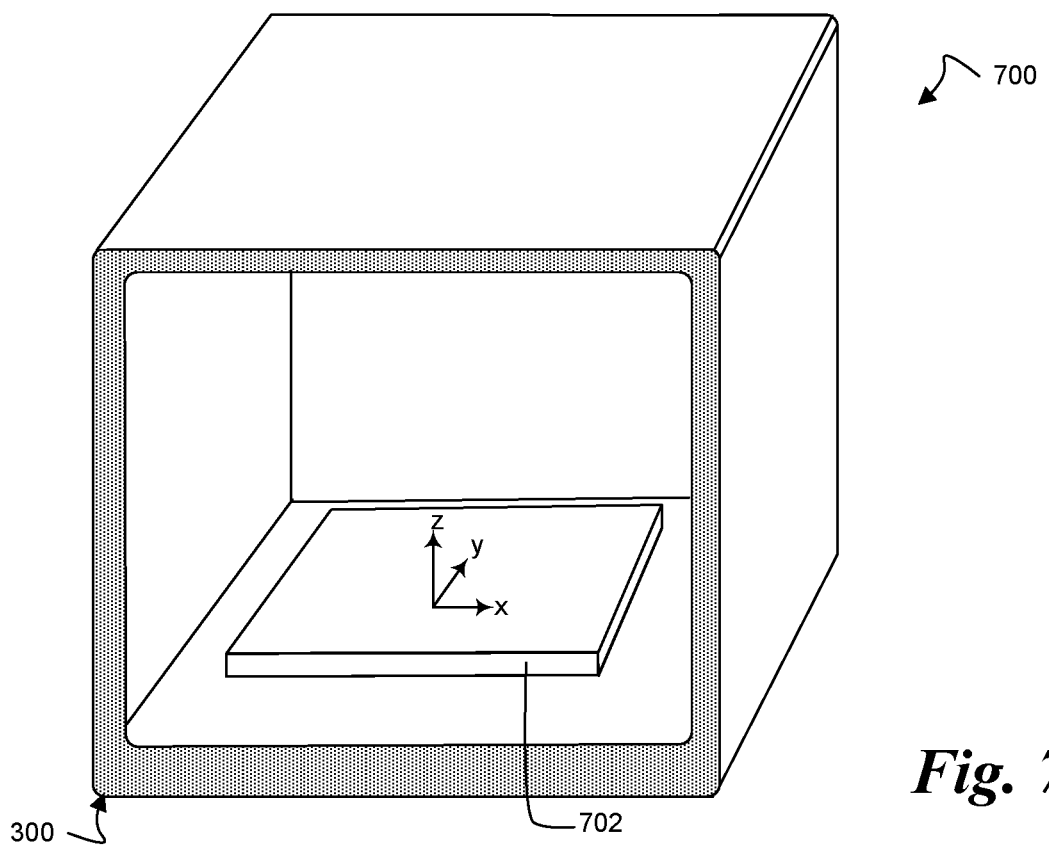
FIG. 7 is block diagram of an embodiment of a mobile carrier including one or more vibration monitoring sensors.

FIG. 7 illustrates an embodiment of a mobile carrier 700 including one or more vibration monitoring sensors. In mobile carrier 700, one or more semiconductor wafers 404 are stacked in the interior of mobile carrier 300 for transport between process equipment modules. A three-axis vibration sensor 702 is positioned in the interior chamber of the carrier, on or near the carrier floor, to detect vibration of the mobile carrier, vibration of the parts (e.g., wafers) inside, vibration of process equipment modules to which the mobile carrier 700 is mated, and vibration in the environment. For instance, vibration sensor 702 can be used to detect 3-axis vibration and check motion stability when carrier 700 moves along the track 110 (see FIG. 1B). Other embodiments of carrier 700 can have more vibration sensors than shown, can have different vibration sensors than shown, and can position them differently than shown.

Figure 8:
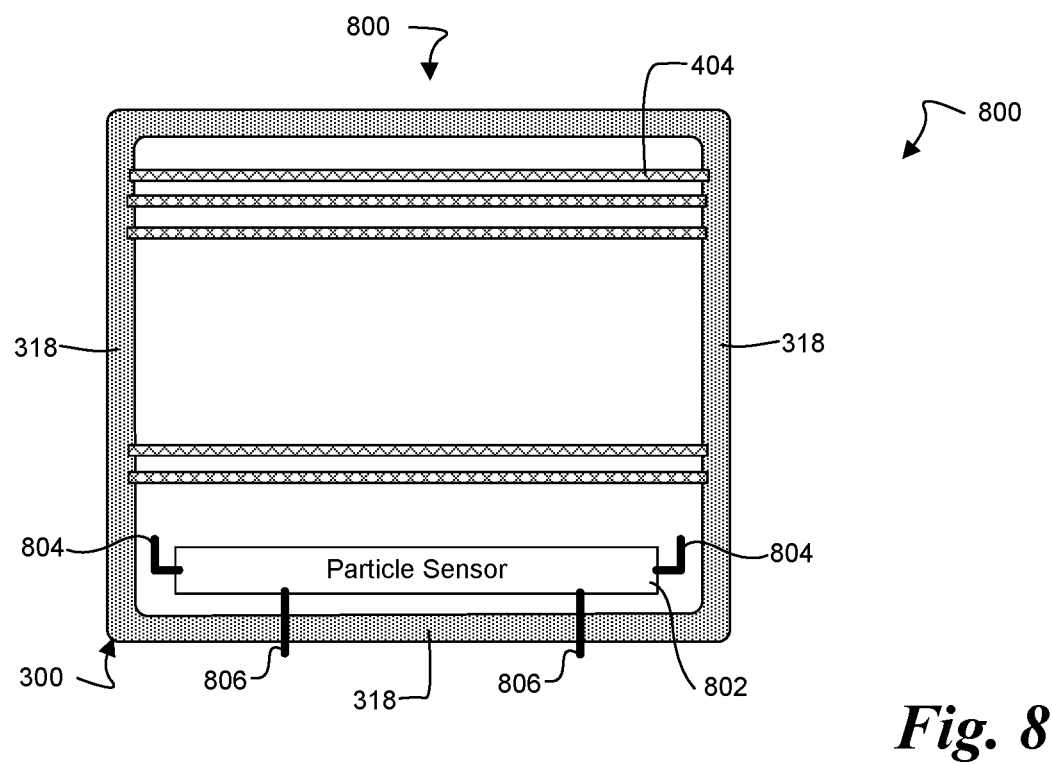
FIG. 8 is block diagram of an embodiment of a mobile carrier including one or more particle monitoring sensors.

FIG. 8 illustrates an embodiment of a mobile carrier 800 including one or more particle monitoring sensors. In mobile carrier 800, one or more semiconductor wafers 404 are stacked in the interior of mobile carrier 300 for transport between process equipment modules. A particle sensor 802 is positioned in the interior chamber of the carrier, on or near the floor. Sensor 802 includes sampling tubes 804 fluidly coupled to the sensor and to the interior of the carrier to draw in air from the interior of the carrier for measurement. Sensor 802 also includes sampling tubes 806 that extend through the bottom sidewall 318 to fluidly couple the sensor to the exterior of the carrier so that it can draw in air from the exterior for measurement—for instance ambient air from the facility or air from a process equipment module to which the carrier was coupled. The sensor can thus detect particle contamination inside the carrier or particle contamination outside the carrier in a machine or in the environment. In other embodiments, the routing of internal and external sampling tubes can be different than shown—sampling tubes 804 and 806 could be routed through sidewalls 318 of carrier 300, for instance—and other embodiments need not sample both internal and external air.

Figure 9:
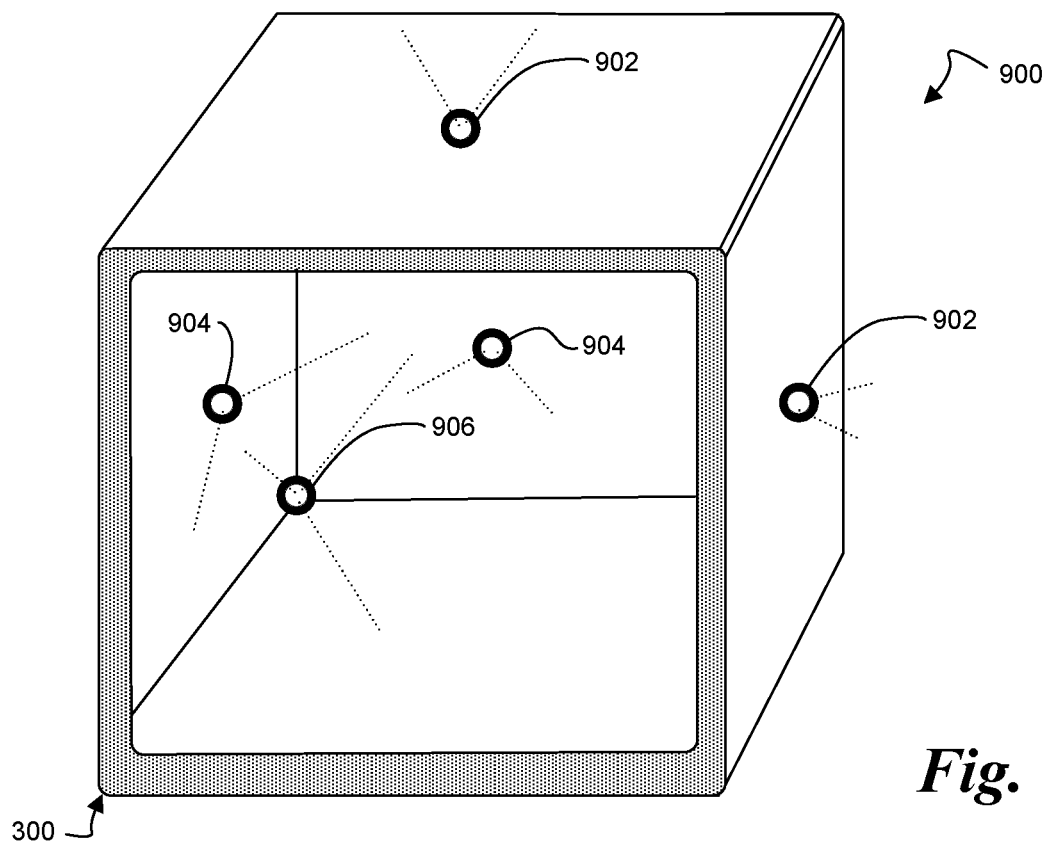
FIG. 9 is block diagram of an embodiment of a mobile carrier including one or more monitoring cameras.

FIG. 9 illustrates an embodiment of a mobile carrier 900 including one or more cameras. In mobile carrier 900, one or more semiconductor wafers 404 are stacked in the interior of mobile carrier 300 for transport between process equipment modules. Cameras can be positioned at various positions in the interior chamber of the carrier: cameras 904 can be positioned on one or more sidewalls, a camera 906 can be positioned in a corner of the interior chamber, or cameras can be positioned on the floor or ceiling. Cameras 902 can also be positioned on the exterior surfaces of the carrier. Cameras 902, 904, and 906 can be used, for example, for visual detection of conditions inside the carrier, visual detection of the carrier's path, or visual detection of the condition of process equipment modules to which the carrier has been mated.

Figure 10:
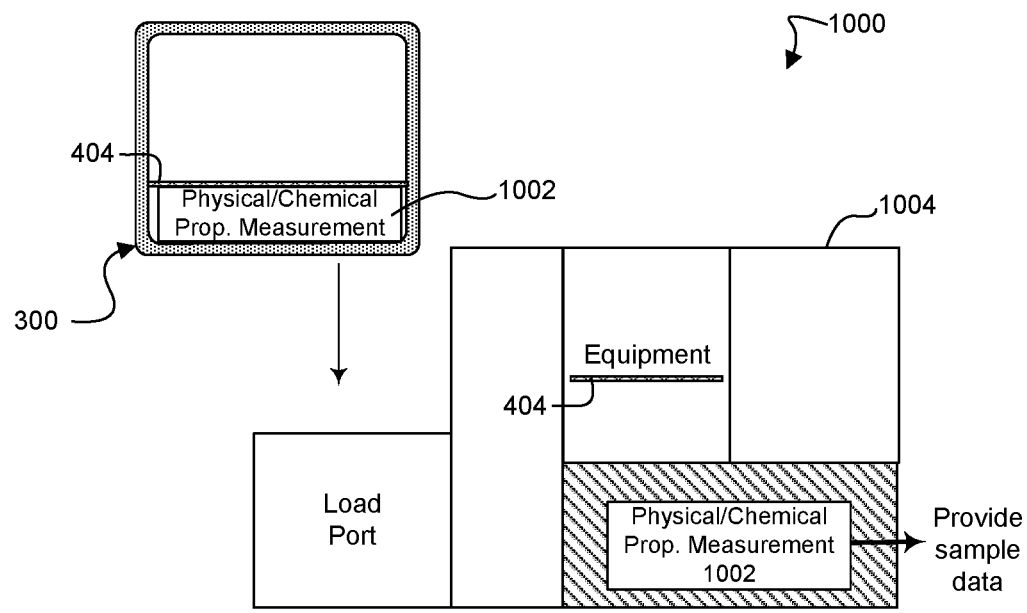
FIG. 10 is block diagram of an embodiment of a mobile carrier including one or more sensors for monitoring physical characteristics.

FIG. 10 is block diagram of an embodiment of a mobile carrier 1000 including one or more sensors for monitoring physical characteristics or chemical characteristics such as product film thickness. In mobile carrier 1000, one or more semiconductor wafers 404 are stacked in the interior of mobile carrier 300 for transport between process equipment modules. In the illustrated embodiment, a physical/chemical property measurement module or sensor 1002 is positioned in the interior chamber of mobile carrier 300 to monitor physical properties (e.g., film thickness, topography, reflective index) or chemical properties (composition, impurity) of material that is deposited on one or more of the wafers 404. But in another embodiment, the measurement module 1002 can be positioned in a smart station 1004 configured to receive a wafer for measurement, so that one or more of the wafers can be carried back to the smart station and transferred to the smart station for measurement instead of being measured inside the mobile carrier.

FIG. 11 illustrates an embodiment of a mobile carrier 1100 including one or more location monitoring sensors that can be used to determine and/or record the position of mobile carrier 1100 within a manufacturing facility. The location monitoring sensors can also determine and/or record the positions of process equipment modules, machine parts, the positions where detection or sampling of the internal or external environment takes place in the facility. Although not illustrated in the figure, one or more semiconductor wafers can be stacked in the interior of mobile carrier 1100 for transport between process equipment modules.

In one embodiment, a Global Positioning System (GPS) unit 1102 that determines its own location, and hence the location of mobile carrier 1100, is positioned on the floor in the interior of the carrier, although in other embodiments GPS unit 1102 could be positioned on the outside of the unit or elsewhere in the inside, so long as it can receive a signal from satellites 1104 to determine its position.

In another embodiment, a Radio Frequency Identification (RFID) reader can be positioned on the top surface of the carrier, for instance on the roof, where it can determine the position of carrier 1100 by reading one or more RFID tags 1106 positioned in the facility. In the illustrated embodiment, RFID tag 1106 is positioned at a known location on track 110 of the transport system used to move the carrier (see FIG. 1B), so that when RFID reader 1104 detects RFID tag 1106 it knows that its position along the track is substantially the same as the position of the RFID tag. In other embodiments, RFID tag 1106 could be positioned at a different location in the facility.

In still another embodiment, a bar code reader 1108 can be positioned on the exterior of the carrier, for instance on the top surface, where it can determine the position of carrier 1100 by reading one or more bar codes 1110 positioned in the facility. In the illustrated embodiment, bar code 1110 is positioned at a known location on track 110 of the transport system, so that when bar code reader 1108 detects bar code 1110 it knows that its position along the track is substantially the same as the position of the bar code. In other embodiments, bar code 1110 could be positioned at a different location in the facility. Other detection methods, such as machine vision, can also be used to determine the location of mobile carrier 1100.

FIGS. 12A-12B together illustrate an embodiment of a mobile carrier 1200 including one or more internal position monitoring sensors; FIG. 12A is a top view, FIG. 12B a side view. In mobile carrier 1200, one or more semiconductor wafers 404 are stacked in the interior of mobile carrier 300 for transport between process equipment modules. But in some cases, it is possible for wafers 404 to become misaligned inside the carrier, for instance as shown by the wafer 404 with the dashed outline, which is too close to the rear wall of the carrier and could become damaged as a result.

To prevent wafer damage, an internal monitoring system can be put in the interior of the carrier to detect the position of the wafers inside. In the illustrated embodiment, a light source 1202 can be positioned on the floor of the carrier along the back wall so that it directs light at a detector 1204 positioned on the ceiling of the carrier along the back wall. With this arrangement, if there is no interruption of the beam emitted by light source 1202 then the wafers 404 are correctly positioned, but if there is a partial or total interruption of the beam, then one of the wafers is out of position. The illustrated embodiment shows only one detector, but in other embodiments multiple detectors, as well as other types of detectors, can be used in additional positions within the interior chamber of the mobile carrier.

FIG. 13 illustrates an embodiment of a mobile carrier 1300 including a sample collection system. In mobile carrier 1300, one or more semiconductor wafers 404 are stacked in the interior of the mobile carrier for transport between process equipment modules.

A sampling bottle or canister 1302 is positioned in the interior of the carrier, on or near the floor of the carrier. Sampling bottle 1302 includes sampling tubes 1304 fluidly coupled to the interior of the sampling canister and to the interior of the carrier to draw in air from the interior of the carrier for collection. Sampling bottle 1302 also includes sampling tubes 1306 that extend through the floor of the carrier to fluidly couple the interior of the sampling bottle to the exterior of the carrier so that it can collect air from the exterior of the mobile carrier—for instance ambient air from the facility or air from a process equipment module to which the carrier was coupled. In an embodiment without sampling tubes 1306, a sample from the exterior can be collected simply by opening the door of the mobile carrier. In other embodiments, the routing of internal and external sampling tubes can be different than shown—sampling tubes could be routed through the sidewalls of container 1300, for instance—and other embodiments need not sample both internal and external air.

In one embodiment sampling bottle 1302 can be pre-vacuumed so that it can draw in samples, but in another embodiment a pump 1308 can be fluidly coupled to the interior of the sampling canister to draw air into the bottle. The samples collected in sampling canister 1302 can be saved for later analysis by an analyzer or sensor within carrier 1300 or by an analyzer or sensor separate from carrier 1300, for instance an analyzer or sensor in a smart station with which mobile carrier 1300 will later dock. Still other embodiments of mobile carrier 1300 can include sensors in addition to the sample collection system. The illustrated embodiment includes airflow sensors 1310 positioned in the interior of the mobile carrier and airflow sensors 1312 positioned on the exterior of the mobile carrier, but any other type of sensors could also be used together with the sample collection system.

FIG. 14 illustrates another embodiment of a mobile carrier 1400 including a sample collection system. In mobile carrier 1400, one or more semiconductor wafers 404 are stacked in the interior of the mobile carrier for transport between process equipment modules.

A trap sampler 1402 having a sorbent 1403 inside is positioned in the interior chamber of the carrier, on or near the floor. In various embodiments, sorbent 1403 can include combinations of granular, wall coatings, or continuous filling sorbents. Each sorbent can have a chemical affinity for one or more particular chemicals, meaning that the exact sorbents used will depend on the number and nature of chemicals to be absorbed and concentrated. Examples of sorbents that can be used include cabopack B, cabopack X, etc.

Trap sampler 1402 includes sampling tubes 1404 that fluidly couple the interior of the trap sampler to the interior of the mobile carrier so that the trap sampler can collect air from the interior of the mobile carrier, and also includes sampling tubes 1406 that extend through the floor of the mobile carrier to fluidly couple the interior of the trap sampler to the exterior of the mobile carrier so that the trap sampler can collect samples from the exterior of the mobile carrier, for instance ambient air from the facility or air from a process equipment module to which the carrier was coupled. In other embodiments, the routing of internal and external sampling tubes can be different than shown—sampling tubes 1304 or 1306 could be routed through the sidewalls of container 1400, for instance—and other embodiments need not sample both internal and external air.

In one embodiment trap sampler 1402 can be pre-vacuumed so that it can draw in samples, but in another embodiment a pump 1408 can be fluidly coupled to the interior of the trap sampler to draw air into the trap sampler. A heater 1410 can also be thermally coupled to the tramp sampler to heat the sorbent inside to help release the compounds captured by the sorbent. The samples collected in trap sampler 1402 can be saved for later analysis by an analyzer or sensor within carrier 1400 or by an analyzer or sensor separate from carrier 1400, for instance an analyzer or sensor in a smart station with which the mobile carrier will later dock. Still other embodiments of mobile carrier 1400 can include sensors in addition to the sample collection system. The illustrated embodiment includes airflow sensors 1410 positioned in the interior of the mobile carrier and airflow sensors 1412 positioned on the exterior of the mobile carrier, but any other type of sensors could also be used together with the sample collection system.

Figure 15:
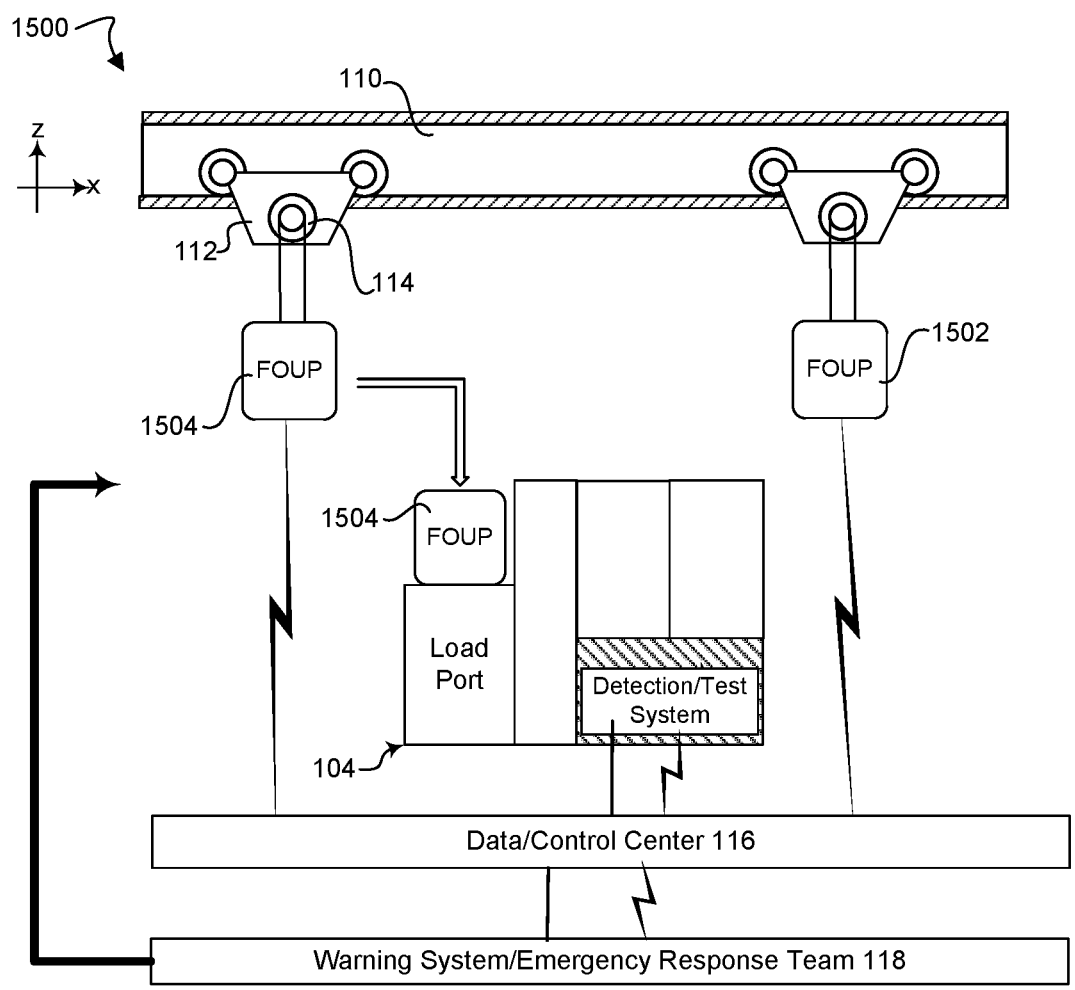
FIG. 15 is a drawing of an embodiment of using multiple mobile carrier systems for monitoring.

FIG. 15 illustrates an embodiment of the use of multiple mobile carriers for monitoring. In the illustrated example, mobile carrier 1502 can include an airborne molecular contamination (AMC) detector together with a location sensor. If mobile carrier 1502 detects AMC or abnormal levels of AMC as it passes over process equipment module 104, it can transmit its position and the detected AMC levels to data/control center 116. Data/control center 116, knowing the location of mobile carrier 1502, can then direct another nearby mobile carrier 1504 with a sampling system (see, e.g., FIGS. 13-14) to dock on the load port of process equipment module 104 and sample the air in that module to see if it is the source of the AMC detected by mobile carrier 1502. In another embodiment, mobile carrier 1504 need not actually dock with process equipment module 104, but can actually just sample the air near module 104.

The above description of embodiments, including what is described in the abstract, is not intended to be exhaustive or to limit the invention to the described forms. Specific embodiments of, and examples for, the invention are described herein for illustrative purposes, but various equivalent modifications are possible within the scope of the invention in light of the above detailed description, as those skilled in the relevant art will recognize.

The terms used in the following claims should not be interpreted to limit the invention to the specific embodiments disclosed in the specification and the claims. Rather, the scope of the invention is to be determined entirely by the following claims, which are to be interpreted using established claim interpretation doctrines.

The invention claimed is:

1. A monitoring system comprising:
    a mobile carrier monitoring apparatus comprising:
        one or more mobile carriers configured to receive items being manufactured in its interior and configured be moved by a transport system to multiple positions within a manufacturing facility,
        a mobile carrier control system positioned in the interior or on the exterior of each mobile carrier,
        one or more sensors positioned in the interior or on the exterior of each mobile carrier, the one or more sensors being coupled to the mobile carrier control system,
        a communication system positioned in the interior or on the exterior of each mobile carrier and communicatively coupled to the at least one sensor and to the mobile carrier control system, wherein the communication system can transmit data from the one or more sensors to a location separate from the mobile carrier,
        an electrical power system positioned in the interior or on the exterior of each mobile carrier and coupled to deliver electrical power to the mobile carrier control system, to the one or more sensors, and to the communication system, and
        a modular coupling system positioned in or on each mobile carrier, the modular coupling system being coupled to the electrical power system, the communication system, and the mobile carrier control system; and
    a smart station including a modular coupling system compatible with the modular coupling system of the mobile carrier.

2. The monitoring system of claim 1 wherein the modular coupling system of the mobile carrier and the modular coupling system of the smart station can include electrical couplings, fluid couplings, communication couplings, or mechanical couplings.

3. The monitoring system of claim 1 wherein:
    the mobile carrier further comprises a sampling system positioned in the interior or on the exterior of each mobile carrier; and
    the smart station includes a smart station operation system and at least one of a detection system, a sampling system, a power supply system, and a wired or wireless communication system, and wherein at least one of the detection system, the sampling system, the power supply system, the wired or wireless communication system, and the smart station operation system are coupled to the modular coupling system of the smart station.

4. The monitoring system of claim 3 wherein the sampling system of at least one of the mobile carrier and the smart station comprises:
    a canister;
    one of more sampling tubes fluidly coupled to the interior of the canister and also fluidly coupled to at least one of the interior of the mobile carrier and the exterior of the mobile carrier.

5. The monitoring system of claim 4 wherein the sampling system further comprises a pump fluidly coupled to the interior of the canister.

6. The monitoring system of claim 3 wherein the sampling system of at least one of the mobile carrier and the smart station comprises:
    a trap sampler including a sorb ent therein;
    one of more sampling tubes fluidly coupled to the interior of the canister and also fluidly coupled to at least one of the interior of the mobile carrier and the exterior of the mobile carrier.

7. The monitoring system of claim 6 wherein the sampling system further comprises at least one of:
    a pump fluidly coupled to the interior of the trap sampler; and
    a heater thermally coupled to the trap sampler to heat the sorbent inside the trap sampler.

8. The monitoring system of claim 3 wherein the detection system in the smart station and the one or more sensors in the mobile carrier can each include:
    an airborne molecular contamination analyzer;
    a temperature sensor including one or more temperature probes;
    an airflow sensor;
    a sensor that measures one or more of water ($H_2O$), oxygen, temperature and humidity;
    a vibration sensor;
    a particle sensor;
    a camera;
    a sensor for measuring physical or chemical characteristics;
    a location sensor; or
    an internal position sensor.

9. The monitoring system of claim 3 wherein the communication system of the mobile carrier and the communication system of the smart station can communicate wirelessly or by wire to a location separate from the mobile carrier or the smart station.

10. The monitoring system of claim 1, further comprising a sampling system positioned in the interior or on the exterior of each mobile carrier.

* * * * *